United States Patent [19]

De Winter-Scailteur

[11] Patent Number: 5,252,537
[45] Date of Patent: Oct. 12, 1993

[54] LONG-LIFE CUT FLOWERS AND METHOD OF TREATMENT FOR OBTAINING SUCH FLOWERS

[75] Inventor: Nadine De Winter-Scailteur, Brussels, Belgium

[73] Assignee: SARL Compagnie Du Nord, Wormhout, France

[21] Appl. No.: 659,300

[22] PCT Filed: Sep. 6, 1990

[86] PCT No.: PCT/BE90/00051
 § 371 Date: May 2, 1991
 § 102(e) Date: May 2, 1991

[87] PCT Pub. No.: WO91/03160
 PCT Pub. Date: Mar. 21, 1991

[30] Foreign Application Priority Data

Sep. 11, 1989 [FR] France .................. 89 12201

[51] Int. Cl.$^5$ ............................. A01N 3/02
[52] U.S. Cl. ........................ 504/114; 428/17; 428/24
[58] Field of Search ............ 71/68; 428/17, 24; 504/114

[56] References Cited

U.S. PATENT DOCUMENTS

| | | | |
|---|---|---|---|
| 547,227 | 10/1895 | Pfitzer | 71/68 |
| 3,895,140 | 7/1975 | Sheldon et al. | 428/22 |
| 4,808,447 | 2/1989 | Baker | 428/17 |
| 4,828,890 | 5/1989 | Tiedeman et al. | 428/22 |

FOREIGN PATENT DOCUMENTS

| | | |
|---|---|---|
| 1354279 | 1/1964 | France . |
| 2196829 | 3/1974 | France . |
| 54-010033 | 1/1979 | Japan . |
| 62-95135 | 5/1987 | Japan . |

OTHER PUBLICATIONS

The Merck Index, 10th Edition, Merck & Co. Inc., Rathway, N.J. p. 4209 (1983).

Primary Examiner—Glennon H. Hollrah
Assistant Examiner—B. Bembenick
Attorney, Agent, or Firm—James Creighton Wray

[57] ABSTRACT

Long-life cut flowers characterized in that their tissue water is replaced with a substance, particularly polyethylene glycol (PEG), which is unsuited to the metabloism of saprophytic agents, and method of treating cut flowers to obtain these long-life flowers.

6 Claims, No Drawings

LONG-LIFE CUT FLOWERS AND METHOD OF TREATMENT FOR OBTAINING SUCH FLOWERS

BACKGROUND OF THE INVENTION

For a number of years attempts have been made to create artificial flowers, made of paper, fabrics or plastic, to satisfy the need for decoration, when conditions are such that it is not possible to satisfy this need with natural flowers, for climatic or economic reasons.

Artificial flowers are far from reproducing the vividness and the beauty of the fresh natural flower.

on the other hand, the natural flower, like any other plant organ, is subject to the decomposition of the tissues which have ceased metabolizing. Saprophytic organisms (bacteria, fungi, etc.) are responsible for the change in the floral qualities and for the final decomposition of the organic matter.

Until now, in order to obtain a prolongation of the floral qualities of natural flowers, attempts have been made to produce dried flowers or to preserve their appearance by immersion in a dye bath containing glycerine.

Thus, in a closely related but different field for preserving boughs or branches of ligneous plants, according to French Patent No. 1,354,279, the boughs are soaked in a bath of monoethylene glycol to prevent the plant from drying.

Furthermore, in U.S. Pat. No. 4,828,890 there is a description of a process for increasing the resistance to the phenomenon of "porelage" (or exudation) of plants which are treated with glycerine for their preservation. This concerns particularly exotic plants such as palms, by employing the perfusion method consisting of a uniform diffusion of a preservative liquid, i.e. one which replaces part of the water present in the cells. Solutions based on glycerine, polyethylene glycol or propylene glycol are employed as preservative liquids.

None of these methods is actually employed for preserving cut flowers.

In fact, the only possibility of preserving the matter constituting the plant tissues of the flowers consists in preventing the destructive action of the decomposition agents by placing them in an inhospitable or abiotic medium. This involves a virtually complete absence of water.

SUMMARY OF THE INVENTION

The subject of the invention relates to the long-term preservation of cut flowers, another subject of the invention being a treatment for obtaining such cut flowers of long duration, i.e. continually maintaining their decorative properties of apparent freshness.

The long-life cut flowers according to the invention are distinguished by the fact that the tissue water of the fresh flowers is wholly replaced with an inalterable substance capable of preserving the flowers in a structural state which is extremely close to the fresh appearance as much in respect of the shape, the volume and the plasticity, as the color and even possibly of the scent.

Another subject of the invention is a treatment of natural flowers whose objective is to maintain continually their decorative properties of apparent freshness.

The treatment of the natural flowers according to the invention is distinguished by the replacement of the tissue water of the flowers with substances which are inappropriate to the metabolism of the saprophytic agents, and which are inalterable and capable of preserving constant physicochemical characteristics, thus making it possible to preserve flowers in a structural state extremely close to the fresh appearance as much in respect of the shape, the volume and the plasticity, as the color and even possibly the scent.

The treatment of the natural flowers according to the invention is distinguished in that it comprises a dehydration stage ensuring a perfect structural maintenance of the tissues, followed by an infiltration stage, itself followed by a draining and drying stage.

In addition, the treatment of the natural flowers according to the invention is distinguished in that the tissue water is progressively absorbed into the pores of a molecular sieve and replaced with a polymer of low molecular weight, soluble in water and in some organic solvents such as polyvinylpyrrolidone, polyvinyl alcohol, cellulose acetate, benzyl or ethyl acetate, collodion or nitrocellulose.

More particularly, the treatment of natural flowers according to the invention is distinguished in that the tissue water is replaced with polyethylene glycol (PEG) of general formula $H-(OCH_2CH_2)n-OH$.

Other characteristics and advantages of the treatment of natural flowers according to the invention will emerge from the description of an embodiment of such a treatment.

DETAILED DESCRIPTION OF THE INVENTION

In a first embodiment of a treatment of natural flowers according to the invention, by way of example, fresh flowers which are not too closed and not too opened are installed in a flower-holder grid so that they are well supported without touching each other.

This flower-holder grid is made up of a trellis cage of the kind employed for cultivation and flower arrangements, enabling the flowers to be supported in a determined, preferably vertical, position. The treatment troughs are preferably provided with a drainage pipe.

Flowers which are particularly suitable for such a treatment are roses, peonies, camellias, marigolds, globe flowers, orchids, dahlias, carnations phloxes, summer chrysanthemums, hollyhocks, and the like, and other species with many petals or a fairly rigid structure.

This flower-holder grid filled with flowers to be treated is deposited in a receptacle specially provided for this purpose, packed with a bed of molecular sieve with a porosity ranging from 3 to 5 angstroms over a thickness of 2 cm or more, so that a physical contact is ensured between the sieve and the petals. The thickness varies as a function of the quantity of flowers and as a function of the quantity of water which they release.

Molecular sieves are metal aluminosilicates which have a crystalline structure consisting of an assembly of tetrahedra. The tetrahedra are made up of 4 oxygen atoms which occupy the summits surrounding either 1 silicon atom or an aluminum atom placed in the center. Compensating cations (sodium, potassium) make the whole electrically neutral. The whole forms an assembly of small cells (or pores) of uniform and known size, in which a molecule of smaller size can be trapped by the phenomenon known as adsorption.

The crystalline structure can be represented by the formula: $Na_{12}(AlO_2)_{12}(SiO_2)_{12}.xH_2O$ in the case of the zeolite of type 3 Å, 4 Å and 5 Å (angströms).

The internal active surface area of the beads is from 600 to 700 m² per gram; they can adsorb from 20 to 30% of their own weight of water.

To ensure the dehydration of the fresh natural flowers the mixture of organic solvents is poured onto the whole until the level exceeds the level of the flowers by about 2 cm.

While the petals remain mechanically supported by the liquids filling the cells, the tissue water is replaced progressively and gradually by the organic solvents. The water molecules are progressively adsorbed into the small cells or pores of the molecular sieve. All the other molecules whose volume is greater than the small cell are therefore not retained.

The receptacle is closed hermetically and the solvents are left to act for at least 12 hours in the case of flowers of small volume, with relatively loosely packed petals, and up to 24 hours in the case of flowers with dense and closely packed petals.

At the end of the dehydration, when the flowers have become completely transparent and colorless, the grid containing the flowers is taken out and the solvents are allowed to drain out in order then to transfer the grid with the flowers to a new receptacle for the infiltration stage. The spent solvents are anhydrous and are recovered for subsequent use. The molecular sieve employed and saturated with water can be regenerated by aeration and heating.

The receptacle for the infiltration stage also contains a layer of molecular sieve enabling a possible quantity of residual water to be trapped. The molecular sieve has a preferred porosity of 4 angströms as previously, thus ensuring a dehydration which is as perfect as possible during all the stages.

The receptacle is then filled with a mixture of anhydrous solvents and of PEG (polyethylene glycol) in proportions which depend on the structure of the flower. These solvents promote the entry of the replacement product.

Since PEG 1000 cannot be employed in the solid state, it requires predissolution in anhydrous organic solvents which will be of the same kind as those employed for the dehydration, in order to promote the exchanges within the cells. The criteria for choosing these solvents are chiefly their ability to dissolve the PEGs, their ability to enter the cell, their innocuousness towards the cellulosic matter forming the cell walls, miscability with water and the degree of ultimate evaporability.

Use is preferably made of cellosolve or monomethylene glycol monomethyl ether, mixed with acetone in proportions which can vary from 50/50 to 70/30.

As for the choice of the PEG to be employed, a molecular weight will be sought which is appropriate to the final structure state, the latter being proportionately stiffer the higher the molecular weight. An excessively low molecular weight will not offer a sufficient mechanical support to reproduce the turgidity, while an excessively high weight makes the petals brittle. Good plasticity properties are obtained with a mixture of PEG 1000 and PEG 400, whose respective proportions depend on the anatomical structure of the flower to be treated. Thus, proportionally more PEG 1000 will be needed for a peony or a marigold than for a rose.

The percentages vary from 8 to 15 parts of PEG 400 and 45 to 70 parts of PEG 1000 per 100 parts of mixture of polymers. The concentration of the PEGs relative to the solvents varies from 60/65% of PEGs per 35 to 40% of solvents.

0.5 to 1 part of diethylene glycol is optionally added as a surfactant or plasticizing solvent.

Dyes are also added to this mixture as a function of the shades to be obtained. These generally involve acid dyes intended for dyeing acrylic fibers, soluble in the solvents employed and fastening well to the matter employed.

The receptacle is closed hermetically to avoid evaporation. The solution is allowed to act for at least 12 hours, and up to 24 hours, depending on the type of flowers to be infiltrated. Heating the bath to 50/60° C. increases the rate of the process 3 to 4-fold.

Thus, by way of an exemplary alternative embodiment, the infiltration stage can be carried out in two steps, mixtures of increasing concentration being allowed to act in succession, e.g. the first having a concentration of 50% of PEG, the second at a concentration of 70%.

The solvents polymers mixture will gradually replace the intracellular solvent introduced in the dehydration stage until an equilibrium is established between the internal solution and the external solution. At this time the tissues of the petals contain PEG 400, PEG 1000 and solvents in a proportion corresponding to 80% of the fresh weight of the flower, the remainder corresponding to the cellulosic structural matter.

This is then followed by the draining and drying stage, to remove the residual part of the solvents so that the polymers resume their solid state, without spoiling or changing the anatomical structure of the petals.

To this end, the flower-holder grid with the infiltrated flowers is deposited on a new molecular sieve, this time with a preferred porosity of 10 angstroms, whose crystalline structure can be represented by the formula $Na_{86}(AlO_2)_{86}(SiO_2)_{106} \cdot xH_2O$.

The sieve adsorbs the water and the organic solvents of low molecular weight while supporting the petals mechanically and prevents them from distorting.

Once dried, the flower reabsorbs a little moisture of atmospheric origin, and this increases its suppleness and its plasticity.

80% of the average fresh weight is restored after treatment.

If initially one has 10 fresh roses with an average weight of 55 g, one obtains:

after drying in air an average weight (dry matter) of 15 g, which means a dry weight of 27% and a water weight of 73% after infiltration before drying an average weight of 58 g after infiltration and drying an average weight of 46 g.

The replacement of 40 g of water with 31 9 of polymer within the tissues is deduced therefrom.

After treatment the petals have a tensile strength which is fairly close to that of the fresh petals.

The folding resistance, expressing the suppleness and capable of being measured by the breaking angle, is close to that of the fresh flowers. Within fresh rose petals it approaches 180°; within infiltrated petals it varies from 170° to 180°.

In another embodiment of the treatment of natural flowers according to the invention it is possible to employ natural flowers which have been dried, for example merely by dehydration in dry air. In this case the petals of the flowers lose their anatomical structure and exhibit distortions due to the massive removal of water with a shrinkage in volume.

To restore their initial volume to the dried flowers, the dried flowers are placed on a grid which is introduced into a receptacle as in the second stage of the preceding treatment according to the invention.

The receptacle is then filled, as before, with a mixture of solvents, generally of methylglycol, diethylene glycol and polyethylene glycol.

As the drying greatly impairs the natural pigments of the flowers, dyes exhibiting a good miscability with the above products, such as textile dyes for acrylic fibers, are introduced into the mixture.

An example of the bath composition is the following:
methylglycol 62%
diethylene glycol 5%
polyethylene glycol 24%
monopropylene glycol 5%
water 4%
dyes 1 ml/l.

The bath is heated to about 90° C., slightly higher if the flowers are in buds, the level of the bath exceeding the level of the flowers by at least 5 cm. The flowers are left to soak at constant temperature until the volume and optimum opening of the bud are perfectly reconstituted.

The procedure is then as before: the basket or the grid are taken out of the bath and allowed to drain and dry to remove the remaining part of the solvents from the flowers, preferably at a temperature of 40° C.

The coloring obtained by means of the dyes introduced with the polymer/solvents mixture is uniform and durable. It can be ascertained by microscopic inspection that the cells of the floral tissues are colored uniformly by the pigmented PEG, which provides additional proof of its entry into the tissues by infiltration. Microscopic sections show at least 75% of the cells infiltrated with colored matter.

This method also makes it possible to produce bleached flowers reproducing the natural vividness of white flowers. The technique consists in adding from 1 to 10% of aqueous hydrogen peroxide and 0.1 to 0.5% of acetic acid during the infiltration process carried out without any dyes. These products are introduced at the end of the infiltration process and are left in contact for 2 to 3 hours. Rinsing with acetone containing 10% of aqueous hydrogen peroxide is necessary before the drying stage.

I claim:

1. Method of treatment of cut flowers, either fresh or dried according to a known treatment, with a view to replacing their tissue water with a substance which is inappropriate to the metabolism of the saprophytic agents, which comprises a dehydration stage when starting with the fresh flowers, followed by an infiltration stage wherein the dehydration stage takes place by adsorption of the molecules of tissue water by means of a molecular sieve having a medium composed of organic solvents in which the flowers to be treated are immersed and wherein after the optional dehydration stage the dehydrated or dried flowers undergo a treatment of infiltration by means of a molecular sieve with a mixture of an anhydrous solvent and of a polymer of low molecular weight, wherein the anhydrous solvent comprises a mixture of cellosolve or monomethylene glycol monomethyl ether with acetone and wherein the polymer comprises a mixture of PEG 1000 and PEG 400.

2. Method as claimed in claim 1, wherein the molecular sieve has a porosity of 3 to 5 angstroms.

3. Method according to claim 1 or 2, wherein the molecular sieve consists of aluminosilicates of general formula $Na_{12}(AlO_2)_{12}(SiO_2).xH_2O$.

4. Method as claimed in claim 1, wherein the anhydrous solvent consists of a 50/50 to 70/30 mixture of cellosolve or monomethylene glycol monomethyl ether with acetone.

5. Method as claimed in claim 1, wherein the infiltration product is a mixture of PEG 1000 and PEG 400 in a proportion of 8 to 15 parts of PEG 400 and 45 parts of PEG 1000 per 100 parts of mixture of polymers.

6. Method as claimed in claim 1, wherein the infiltrating mixture is made up of 60 to 65% of PEG per 35 to 40% of anhydrous solvent.

* * * * *